United States Patent
Wang et al.

(10) Patent No.: US 6,221,097 B1
(45) Date of Patent: Apr. 24, 2001

(54) LUBRICATED SLEEVE MATERIAL FOR STENT DELIVERY

(75) Inventors: Lixiao Wang, Maple Grove; Dachuan Yang; Jianhua Chen, both of Plymouth; The Thomas Trinh Tran, Coon Rapids, all of MN (US)

(73) Assignee: SciMed Life System, Inc., Maple Grove, MN (US)

( * ) Notice: Subject to any disclaimer, the term of this patent is extended or adjusted under 35 U.S.C. 154(b) by 0 days.

(21) Appl. No.: 09/273,520

(22) Filed: Mar. 22, 1999

(51) Int. Cl.$^7$ .............................. A61F 2/02; A61M 25/10
(52) U.S. Cl. ................................ 623/1.11; 606/108
(58) Field of Search ........................... 606/108, 191, 606/192, 194; 604/96, 103; 623/1.11

(56) References Cited

U.S. PATENT DOCUMENTS

| | | | |
|---|---|---|---|
| 3,892,314 | 7/1975 | Semp | 206/363 |
| 4,773,902 | 9/1988 | Lentz et al. | 604/265 |
| 4,950,227 | * 8/1990 | Savin et al. | 604/8 |
| 5,409,495 | * 4/1995 | Osborn | 606/108 |
| 5,534,007 | * 7/1996 | St. Germain et al. | 606/108 |
| 5,634,928 | 6/1997 | Fischell et al. | 606/108 |
| 5,690,644 | * 11/1997 | Yurek et al. | 606/108 |
| 5,702,418 | * 12/1997 | Ravenscroft | 606/198 |
| 5,843,090 | * 12/1998 | Schuetz | 606/108 |
| 5,843,092 | * 12/1998 | Heller et al. | 606/108 |
| 5,951,569 | * 9/1999 | Tuckey et al. | 606/108 |
| 5,980,530 | * 11/1999 | Willard et al. | 606/108 |
| 5,980,533 | * 11/1999 | Holman | 606/108 |
| 5,989,280 | * 11/1999 | Euteneuer et al. | 606/198 |

FOREIGN PATENT DOCUMENTS

| | | | |
|---|---|---|---|
| 0 442 657 A2 | 2/1990 | (EP) | 61/6 |
| 0 688 545 A1 | 6/1995 | (EP) | 61/6 |

* cited by examiner

*Primary Examiner*—Gene Mancene
*Assistant Examiner*—Michael B. Priddy
(74) *Attorney, Agent, or Firm*—Vidas, Arrett & Steinkraus

(57) ABSTRACT

The present invention relates to a stent delivery system in which a catheter carries on its distal end portion a stent which is held in place around the catheter prior to and during percutaneous delivery by means of one, and preferably two, end sleeves. The sleeves are positioned around the catheter with one end portion of each sleeve associated thereto. The other end of each sleeve overlaps an end portion of the stent to hold it in place on the catheter in a contracted condition. The present invention provides an improvement with respect to lubrication of the sleeve prior to its assembly with the catheter. A preferred way of lubricating the sleeve is by incorporating a lubricant additive within the sleeve composition.

29 Claims, 1 Drawing Sheet

LUBRICATED SLEEVE MATERIAL FOR STENT DELIVERY

BACKGROUND OF THE INVENTION

Figure 1:
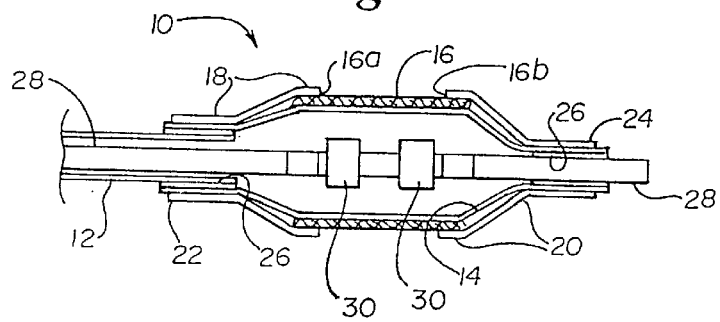
Figure 2:
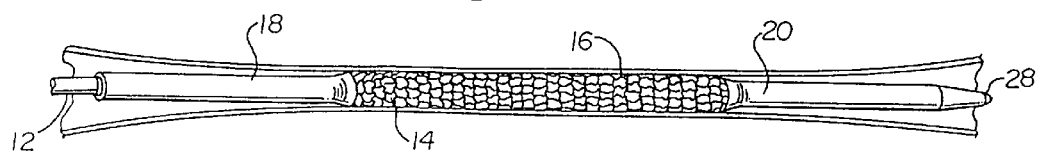

This invention relates to apparatus suitable for stent delivery and implantation.

Generally, stents are implantable devices which are placed within body lumens and the like, such as blood vessels. Stents are typically tubular in form, the diameter of which can be increased for implantation. Stents are usually introduced for implantation percutaneously by means of a catheter.

SUMMARY OF THE INVENTION

In its primary aspect, this invention relates to an improvement in the stent delivery system described in U.S. Pat. No. 4,950,227, entitled "Stent Delivery System" and issued on Aug. 21, 1990. That patent is incorporated herein in its entirety by reference.

The patent relates to a delivery system in which a catheter carries on its distal end portion a stent which is held in place around the catheter prior to and during percutaneous delivery by means of one and preferably two end sleeves. The stent may be self-expanding, such as a NITINOL shape memory stent, or it may be expandable by means of an expandable portion of the catheter, such as a balloon.

The sleeves are positioned around the catheter with one end portion of each sleeve connected thereto. The other end of each sleeve overlaps an opposite end portion of the stent to hold it in place on the catheter in a contracted condition. The sleeves are elastomeric in nature so as to stretch and release the stent when it expands for implantation. In the patent, sometimes a fluid lubricant is added between the sleeve and the balloon on the catheter to facilitate release of the stent.

This invention provides an improvement with respect to lubrication by coating or other wise lubricating the sleeve prior to its assembly with the catheter. A preferred way of lubricating the sleeve is by incorporating a lubricant additive within the sleeve composition. By this is meant that an additive is included within the polymeric composition per se or physically within the matrix of the polymeric composition, such as including discrete dry lubricant particles within matrix pores of a sleeve body.

BRIEF DESCRIPTION OF THE DRAWING(S)

FIG. 1 is a schematic plan view of the distal end portion of a balloon catheter having a stent fixed to the catheter by means of a pair of retaining sleeves, and FIGS. 2, 3, 4 and 5 are schematic views showing expansion of a catheter balloon and stent and the resultant release of the stent from a pair of retaining sleeves.

DESCRIPTION OF PREFERRED EMBODIMENTS

Referring to FIG. 1, a stent delivery system 10 includes a balloon catheter 12 having a balloon 14 fixed to the catheter for remote inflation as is known in the art. Balloon 14 is shown schematically in a somewhat contracted state for clarity of illustration. A stent 16 is positioned about balloon 14 on catheter 12 and retained in position by two overlying retaining sleeves, a proximal one 18 and a distal one 20.

The delivery system catheter may include marker bands 26, an inner shaft 28, and crimp support rings 30 on inner shaft 28.

Stent 16 may be of any known type. In this instance for example it may be a balloon expandable stent of stainless steel, such as the known types which are cut or etched from hypotubes.

Sleeves 18 and 20 are axially fixed along catheter 12 as by an adhesive 26 at 22 and 24, respectively. The sleeves overlap stent 16 at each of the stent ends or margins 16a and 16b as shown.

The sleeve material may be any elastomer such as natural rubber, synthetic rubber, silicone rubber, or a thermoplastic elastomer. Such materials will function in an improved manner if provided with lubrication in order to exhibit a satisfactory releasing effect when the stent is expanded and deployed.

In accordance with this invention it has been found to be desirable to coat the sleeve, at least on the inside but preferably on the inside and outside, prior to its being assembled with the catheter rather than exposing the sleeve to lubricant after it is assembled with the catheter, as in the Savin et al. patent.

Furthermore, the lubricant may be added to a sleeve by (1) coating it before assembly (2) adding the lubricant to the sleeve material during extrusion or (3) by compounding the lubricant with the sleeve material prior to extrusion. All of these can be combined for maximum effectiveness.

A number of lubricants may be added into elastomer or thermoplastic compositions during melt processes or compounding. For example, lubricates suitable for this application, include fluoropolymer powders, graphite; fatty acid esters and amides, hydrocarbon waxes; and silicone masterbatch additive.

EXAMPLE 1

Carbothane, made by Thermedics, or ChronoFlex C, made by TC Biomaterial, was compounded with a hydroxystearamide wax (fatty acid amide) 3% by weight, made by CasChem. The compound was extruded into a tube and then formed into a sleeve. The sleeve exhibited good slippery characteristics. The amide wax can be added into the matrix during the extrusion process as well.

EXAMPLE 2

Carbothane or ChronoFlex was compounded with silicone masterbatch additive, made by Dow Corning. The sleeve formed from this modified material exhibited good slipperiness. Due to the ultrahigh molecular weight of silicone, the modified material may be bonded onto other materials by heat bonding or adhesive bonding.

EXAMPLE 3

Pre-cured natural rubber latex, made by Revertex Chemicals, was used to make a rubber sleeve. The sleeve was treated with sodium hypochloride and hydroxyl chloride to obtain a smooth slippery surface.

EXAMPLE 4

An untreated natural rubber sleeve was coated with a slippery agent to provide slipperiness. The slippery agent was silicone. Other slippery coatings will be readily apparent for this use.

EXAMPLE 5

To ensure the delivery system has the best lesion entry effectiveness, i.e., the smallest entry profile, a hydrophillic coating was applied to the top of the sleeves. This is particularly important with respect to the distal sleeve. Any effective hydrophilic coating can be used in this application. The sleeve performed satisfactorily.

EXAMPLE 6

Formed sleeve tubing was coated with a silicone lubricant by dipping method, the silicone solution was a mixture of MDX4 and DC360, both from Dow Chemicals, in heptane solvent. The concentration was 6% (wt/vol.). The tubing was dipped into this solution for 10 seconds and then dried in room temperature for two hours, further dried at 50° C. in heating oven for four hours to complete the crosslinking. After coating, the tubing was cut into appropriate lengths for the mounting operation as sleeves. The sleeve performed satisfactorily.

EXAMPLE 7

Formed sleeve tubing was coated by a hydrophilic lubricant by dipping. The hydrophilic lubricant solution used was a copolymer PEO-PPO-PEO (Pluronic L101 from BASF) at 10% (wt/vol.) concentration in isopropanol. The tubing was dipped into this solution for 10 seconds then dried in room temperature for about two hours. After coating, the tubing was cut into appropriate lengths for the mounting operation as sleeves. The sleeve performed satisfactorily.

EXAMPLE 8

This example was intended to test a mixture of hydrophilic and hydrophobic lubricants. The solution was mixed with two portions of the lubricants used in Example 6 and Example 7 at 1:1 ratio. The tubing was dipped into this mixture solution for 10 seconds and then dried in room temperature for two hours. Further drying was accomplished in a 50° C. heating oven for about 4 hours. After coating, the tubing was cut into appropriate lengths for the mounting operation as sleeves. The sleeves preferred satisfactorily.

EXAMPLE 9

Formed sleeve tubing was coated by a hydrophilic lubricant by dipping, the hydrophilic lubricant solution used was a low molecular weight polyethylene glycol (PEG, Mn 400 from Aldrich) at 20% (wt/vol.) concentration in ethanol. The sleeve tubing was dipped into this solution for 10 seconds then dried at room temperature for about two hours. After coating, the tubing was cut into appropriate lengths for the mounting operation as sleeves. The sleeves performed satisfactorily.

EXAMPLE 10

Formed sleeve tubing was dipped into a hydrophilic lubricant solution. The solution was a mixture of surfactant, silicones and fatty acid oil in isopropanol, which was 5% Pluronic L101 (BASF) 5% DC360 (Dow Chemicals) and 5% olive oil (Aldrich) in isopropanol (wt/vol.). The sleeve tubing was dipped into this solution for 10 seconds then dried at room temperature for about two hours. After drying, the coated tubing was cut into appropriate lengths for the assembly operation with the catheter as sleeves. The sleeves performed satisfactorily.

EXAMPLE 11

Low molecular weight polyethylene oxide (PEO), copolymers of PEO and PPO, including PEO-PPO-PEO and PPO-PEP-PPO (PPO=polypropylene oxide) at various molecular weights; low molecular weight biodegradable polylactic acid and polycaprolactone, or their copolymers; copolymers of silicone and PEO (Silwet surfactant) at various molecular weights; modified fatty acid such as the polyoxyethylated fatty acid, polysorbates (Tween surfactant); modified castor oil such as PEG 40 castor oil and Cremophor EL 35 may be used as lubricants.

Figure 3:
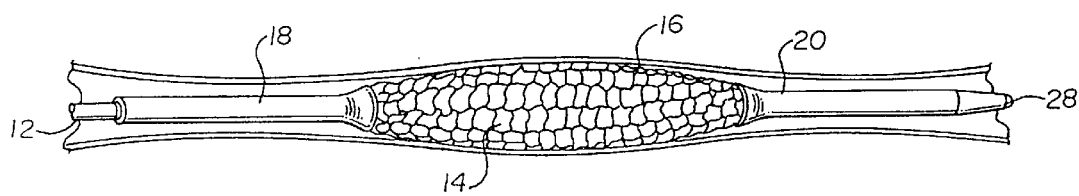
Figure 4:
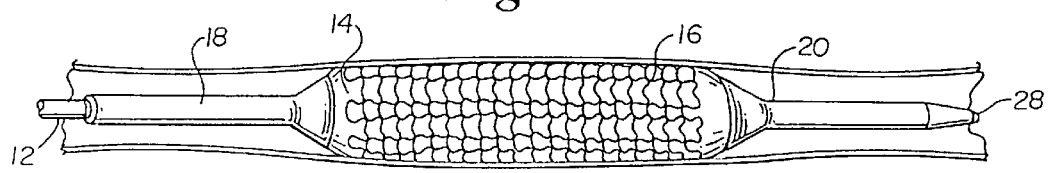
Figure 5:
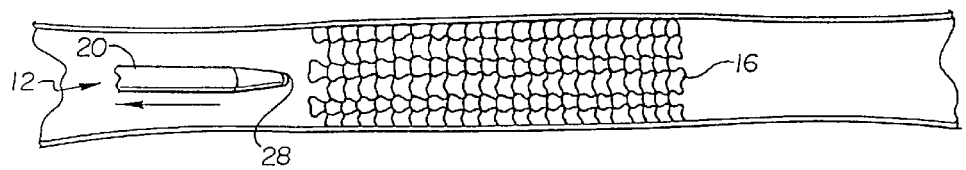

Referring to FIGS. 2, 3, 4 and 5, stent delivery system 10 is inserted percutaneously by known technique into a body lumen or the like. As the stent is positioned (FIG. 2) as required, balloon 14 is expanded (FIGS. 3 and 4). During balloon expansion, stent 16 is also expanded and sleeves 18 and 20 deform elastically to release the stent. The balloon is then deflated by standard technique. The sleeves collapse and catheter 12 with sleeves 18 and 20 is axially removed leaving stent 16 implanted (FIG. 5).

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. In a stent delivery system comprising:
    a catheter including a distal portion constructed and arranged to carry and release a stent;
    a stent positioned around the distal portion of the catheter, the stent having a contracted condition and being expandable to an expanded condition, the stent having two end portions, both end portions lying over the distal portion of the catheter, and
    an elastomeric first sleeve of polymeric composition carried in the region of the distal portion of the catheter and positioned around the catheter, the first sleeve having a first end attached to the catheter and a second end lying over the end portion of the stent which lies over the catheter, the first sleeve fixing the end of the stent on the catheter when the stent is in the contracted condition, the catheter and stent being cooperatively constructed and arranged for expansion of the stent and axial removal of the first sleeve from the margin of the stent upon delivery of the stent for implantation,
    the improvement comprising:
    the first sleeve being a pre-lubricated sleeve, wherein the first sleeve is lubricated with a lubricant additive prior to assembly with the catheter to reduce friction and facilitate release of the stent.

2. The stent delivery system of claim 1 wherein the catheter end portion includes expansible means for expanding the stent.

3. The stent delivery system of claim 2 wherein the expansible means includes a balloon constructed and arranged in cooperation with the catheter for expanding the stent.

4. The stent delivery system of claim 1, further comprising a second pre-lubricated sleeve, the first and second sleeves respectively positioned proximally and distally with respect to the stent proximal and distal end portions, each sleeve having a first end attached to the catheter and a second end overlying one end portion of the stent to separately engage the stent.

5. The stent delivery system of claim 4 wherein the lubricant comprises organic material.

6. The stent delivery system of claim 5 wherein the lubricant is in the form of particles.

7. The stent delivery system of claim 6 wherein the particles are dry.

8. The stent delivery system of claim 4 wherein the lubricant is in the form of particles.

9. The stent delivery system of claim 8 wherein the particles are dry.

10. The stent delivery system of claim 4 wherein the lubricant is a coating.

11. The stent delivery system of claim 4 wherein the lubricant is included within the sleeves during its formation.

12. The stent delivery system of claim 4 wherein the lubricant is included in the composition of the sleeves.

13. The stent delivery system of claim 1 wherein the lubricant additive is comprised of more than one material.

14. The stent delivery system of claim 1 wherein the lubricant comprises organic material.

15. The stent delivery system of claim 14 wherein the lubricant is in the form of particles.

16. The stent delivery system of claim 15 wherein the particles are dry.

17. The stent delivery system of claim 1 wherein the lubricant is in the form of particles.

18. The stent delivery system of claim 17 wherein the particles are dry.

19. The stent delivery system of claim 1 wherein the lubricant is a coating.

20. The stent delivery system of claim 1 wherein the lubricant is included within the first sleeve during its formation.

21. The stent delivery system of claim 1 wherein the lubricant is included in the composition of the sleeve.

22. A method of facilitating the operation of a stent delivery catheter having at least one sleeve encompassing at least one end of a stent carried by the catheter comprising the steps of lubricating the sleeve prior to its assembly with the catheter.

23. The method of claim 22 wherein the lubricant is included within the sleeve composition.

24. The method of claim 22 wherein the lubricant is added by coating at least a portion of the sleeve.

25. The method of claim 22 wherein the lubricant is added during the formation of the sleeve.

26. A method of facilitating the operation of a stent delivery catheter having a first sleeve and a second sleeve encompassing the ends of a stent carried by the catheter comprising the step of lubricating the sleeves prior to their assembly with the catheter.

27. The method of claim 26 wherein the lubricant is included within the sleeves' composition.

28. The method of claim 26 wherein the lubricant is added by coating at least a portion of the sleeves.

29. The stent delivery system of claim 4 wherein the lubricant additive is comprised of more than one material.

* * * * *